(12) United States Patent
Temsamani et al.

(10) Patent No.: US 9,427,455 B2
(45) Date of Patent: Aug. 30, 2016

(54) USE OF THE PAT NANOPEPTIDE IN THE TREATMENT OF AUTOIMMUNE DISEASES

(75) Inventors: Jamal Temsamani, Nimes (FR); Claude Laruelle, Nice (FR)

(73) Assignee: CLL PHARMA, Nice (FR)

( * ) Notice: Subject to any disclaimer, the term of this patent is extended or adjusted under 35 U.S.C. 154(b) by 1715 days.

(21) Appl. No.: 12/736,599

(22) PCT Filed: Apr. 15, 2009

(86) PCT No.: PCT/FR2009/000439
§ 371 (c)(1),
(2), (4) Date: Jan. 3, 2011

(87) PCT Pub. No.: WO2009/150310
PCT Pub. Date: Dec. 17, 2009

(65) Prior Publication Data
US 2011/0098223 A1 Apr. 28, 2011

(30) Foreign Application Priority Data

Apr. 21, 2008 (FR) ...................................... 08 02220

(51) Int. Cl.
*A61K 38/00* (2006.01)
*C07K 16/00* (2006.01)
*A61K 38/08* (2006.01)

(52) U.S. Cl.
CPC ...................................... *A61K 38/08* (2013.01)

(58) Field of Classification Search
None
See application file for complete search history.

(56) References Cited

U.S. PATENT DOCUMENTS

| 4,098,777 | A | | 7/1978 | Veber et al. |
|---|---|---|---|---|
| 4,133,804 | A | | 1/1979 | Bach et al. |
| 4,301,065 | A | | 11/1981 | Bach et al. |
| 5,112,810 | A | | 5/1992 | Nagai et al. |
| 5,808,009 | A | * | 9/1998 | Robinson ............... C07K 16/18 |
| | | | | 530/387.1 |
| 2005/0261194 | A1 | * | 11/2005 | Dardenne et al. ............... 514/16 |

FOREIGN PATENT DOCUMENTS

| EP | 0041019 B1 * | 10/1984 |
|---|---|---|
| FR | 2 513 125 | 3/1983 |
| FR | 2 830 451 | 4/2003 |

OTHER PUBLICATIONS

Godin, Gut. Jul. 1984; 25(7):743-7.*
International Search Report for PCT/FR2009/000439, mailed Oct. 20, 2009.

* cited by examiner

*Primary Examiner* — Jeanette Lieb
(74) *Attorney, Agent, or Firm* — Young & Thompson

(57) ABSTRACT

The invention refers to the use of the PAT nonapeptide which is a thymuline analog in the treatment of autoimmune diseases, in particular of rheumatoid arthritis and intestinal bowel diseases (IBD) such as the Crohn's disease.

10 Claims, 7 Drawing Sheets

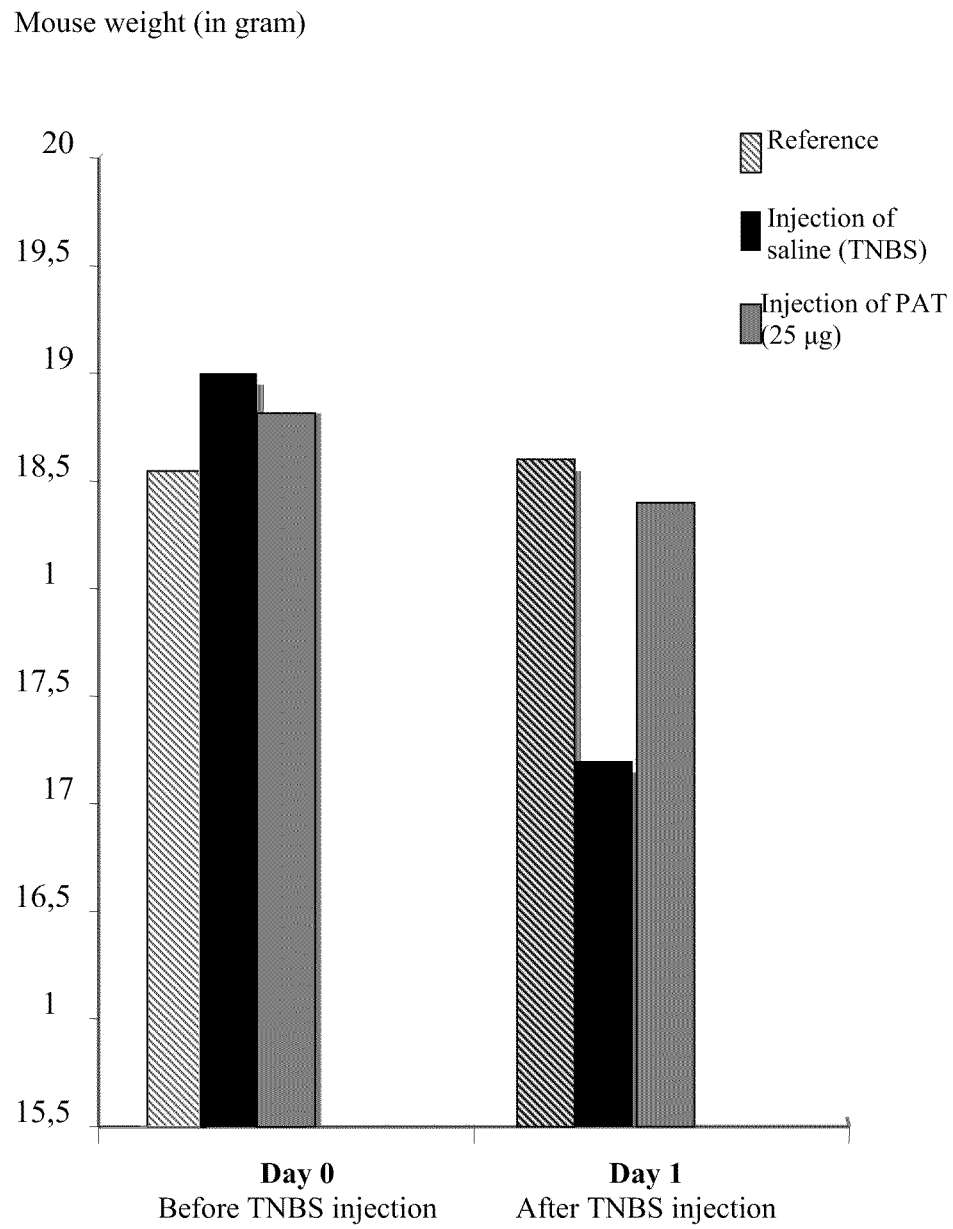
Figure 1: Effect of the PAT nonapeptide on animal weight (in gramm)

Figure 2: Effect of the PAT nonapeptide at a dose of 25 µg / mouse on the reduction of colon inflammation caused by the TNBS.
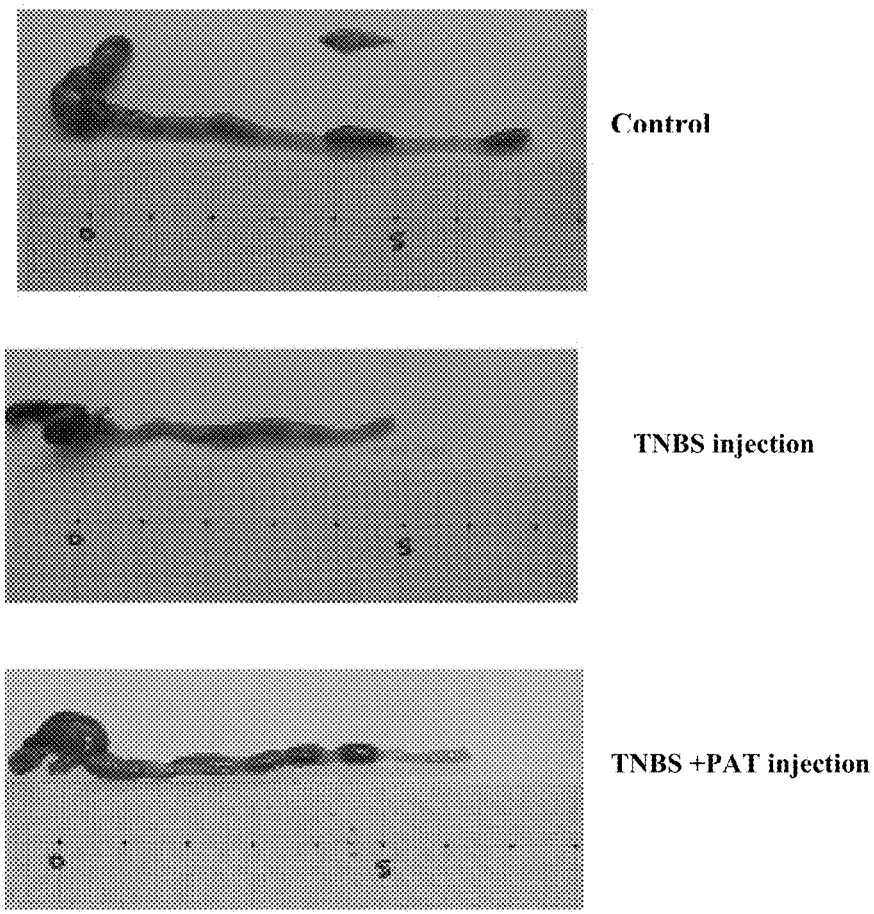

Figure 3: Effect of the PAT nonapeptide on the secretion of pro-inflammatory cytokines. The stimulation rate is determined in comparison to the reference gene
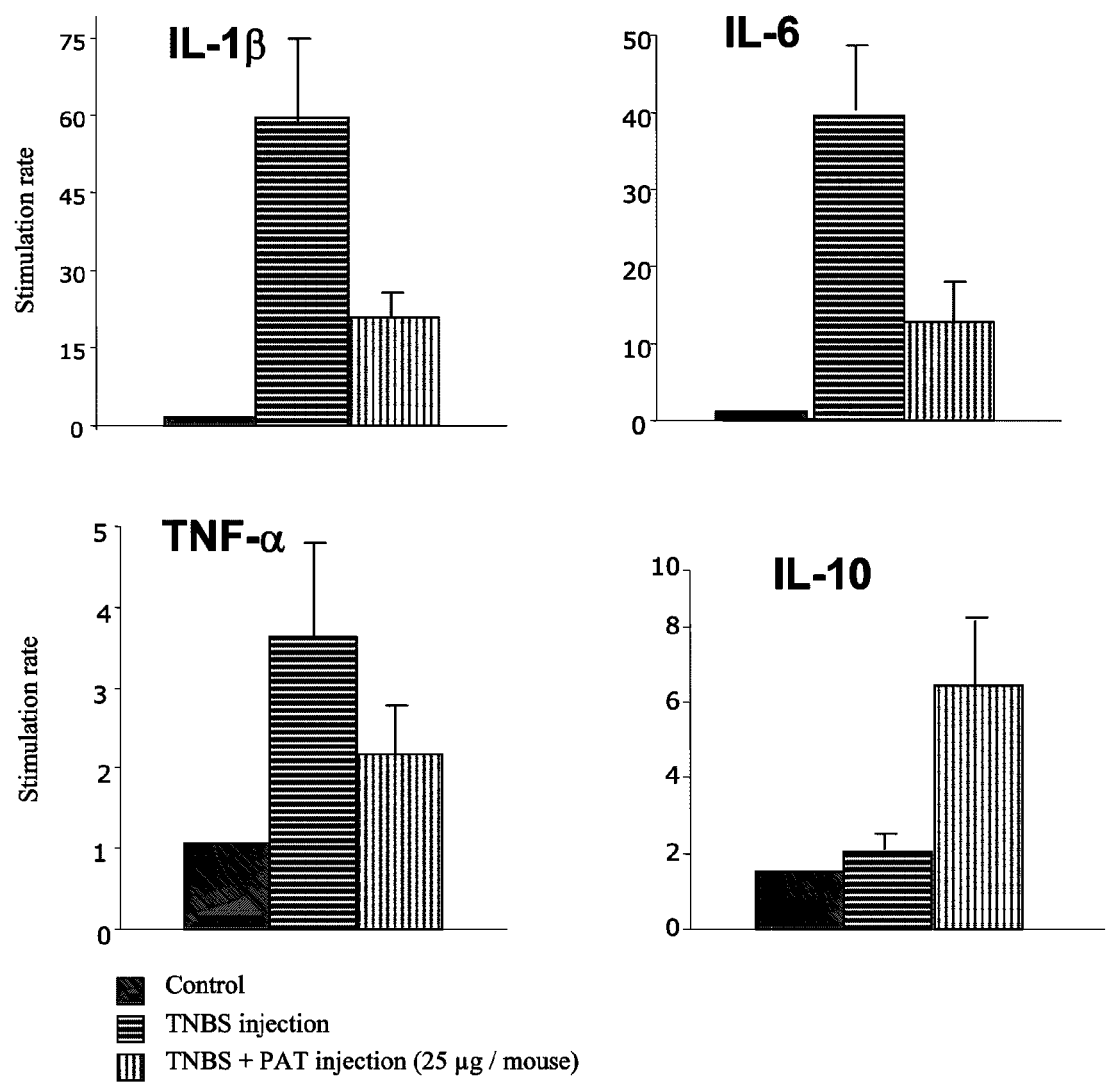

Figure 4 : Effect of the PAT peptide and of the NSAID indomethacin on the leg volume in arthritic rats.
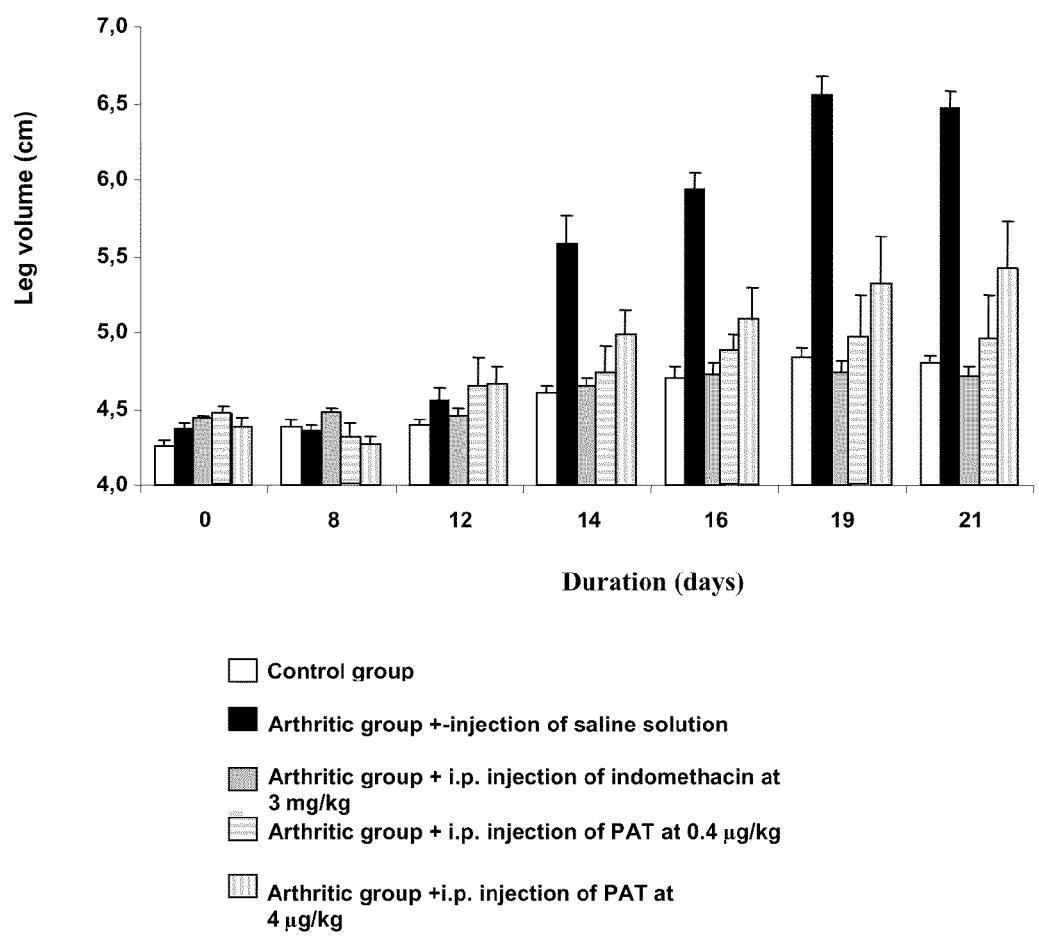

Figure 5 : Effect of the PAT peptide and the NSAID indomethacin on the clinic macroscopic score.
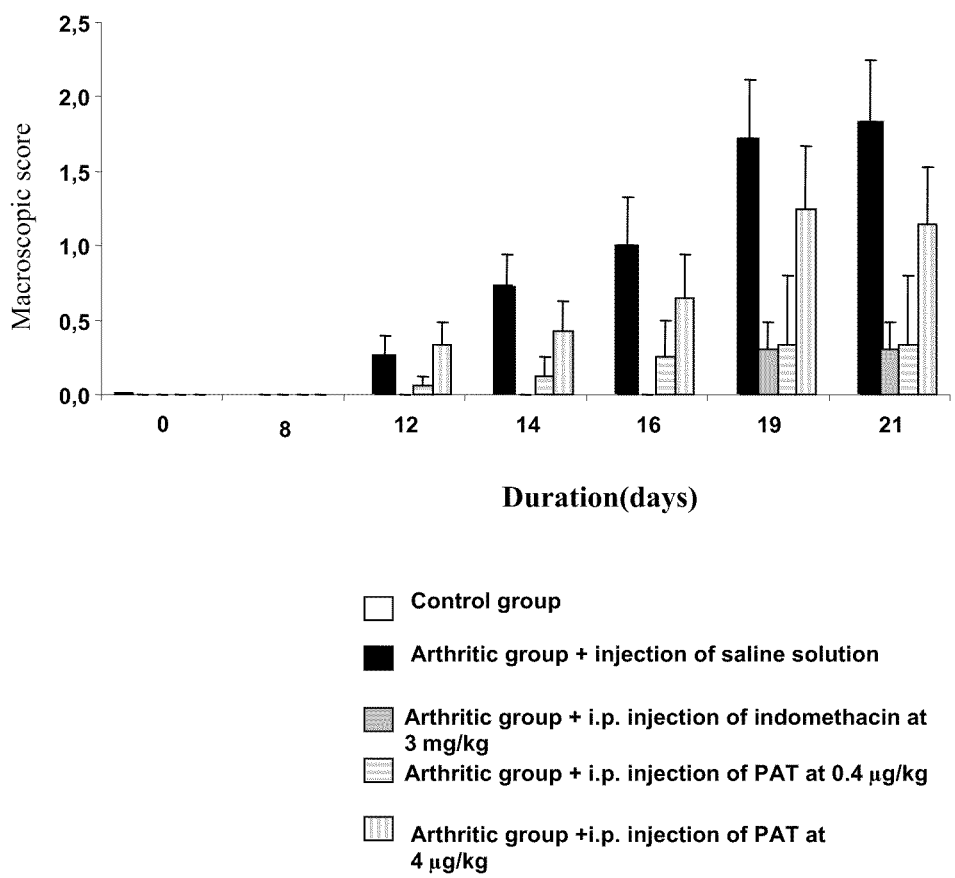

Figure 6 : Effect of the PAT peptide and the NSAID indomethacin on the hypersensitivity measured by the plantar test
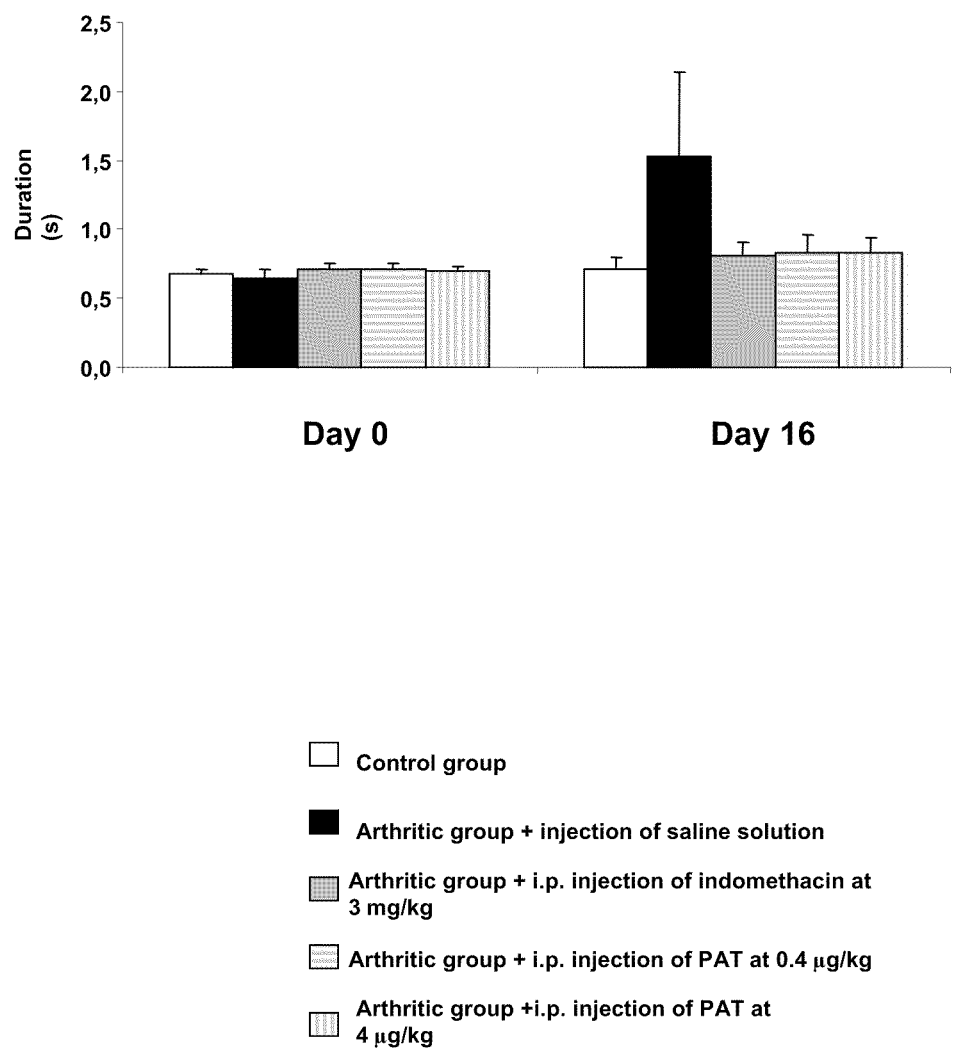

Figure 7: Effect of the PAT peptide and the NSAID indomethacin on the Erythrocyte Sedimentation Rate
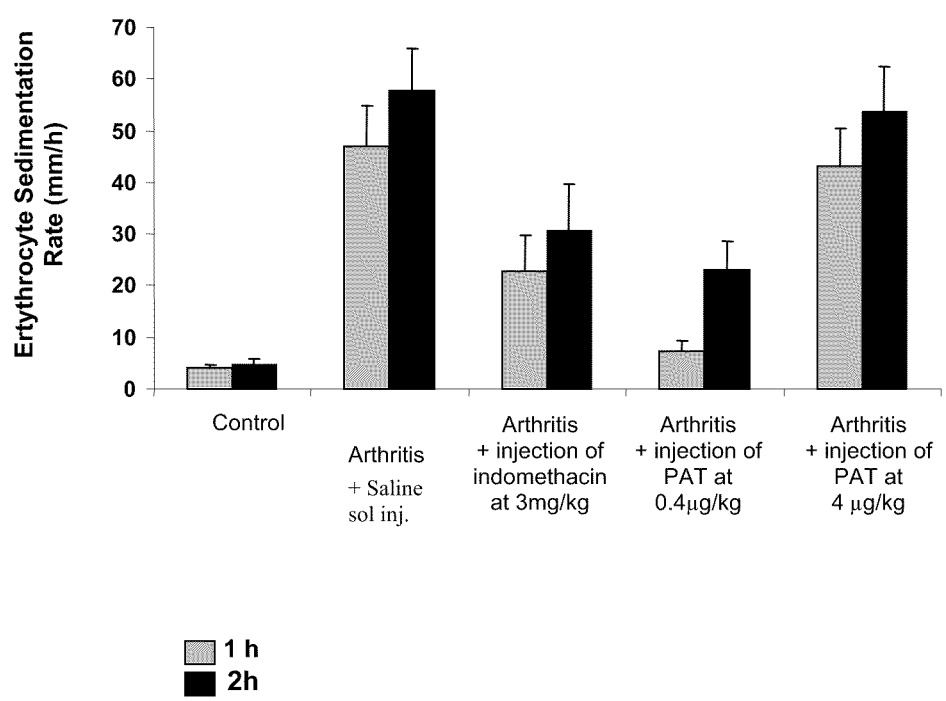

USE OF THE PAT NANOPEPTIDE IN THE TREATMENT OF AUTOIMMUNE DISEASES

This application is the U.S. national phase of International Application No. PCT/FR2009/000439, filed 15 Apr. 2009, which designated the U.S. and claims priority to FR Application No. 0802220, filed 21 Apr. 2008, the entire contents of each of which are hereby incorporated by reference.

FIELD OF THE INVENTION

The invention refers to the use of the PAT nonapeptide in the manufacture of a drug in the treatment of autoimmune diseases.

BACKGROUND OF THE INVENTION

The autoimmune diseases are due to a dysfunction of the immune system which recognizes in an inappropriate way some self components leading to abnormal immunization responses. The body "is attacked" by its own immune system. Today the list of the autoimmune diseases is exhaustive and understands inter alia: inflammatory bowel disease (IBD) such as Crohn's disease and hemorrhagic rectocolitis; multiple sclerosis; psoriatic arthritis; Basedow's disease; rheumatoid arthritis; disseminated erythematous lupus; insulinodependent diabetes, spondylarthritis, etc. Among the autoimmune diseases which represent an urgent medical need, we will describe in a descriptive but nonrestrictive way: Crohn's disease, hemorrhagic rectocolitis, multiple sclerosis and psoriasis. In most autoimmune diseases such as Crohn's disease, psoriatic arthritis, etc, some cytokines as TNF-α induce an attack of healthy tissue and produce various lesions characteristic of each pathology.

Inflammatory bowel diseases (IBD) are diseases characterized by a chronic inflammation which affects the intestines. The physiopathological mechanism common to the IBD is the inflammation of the intestinal mucous membrane. This inflammation is made by an activation of the intestinal immune system which is triggered by both genetic traits and environmental factors. This IBD group includes two great chronic and recurring diseases, which evolve by crisis and which tend to carry on all the life:

Crohn's disease which can affect the whole digestive tract almost from the mouth to the anus and preferentially the final part of small intestine and the beginning of colon. The diagnosis is based on chronic diarrhea, abdominal pain, perianal fistulae or abscesses, slimming and fever. The continuation of the inflammation in Crohn's disease and in ulcerative colitis can be checked partly by an increased secretion of pro-inflammatory cytokines (Reinecker H C et al, Clin. Exp. Immunol 1993; 94: 174-181). According to the same publication, dosage of the pro-inflammatory TNF-α, IL-1-β and IL-6 cytokines from colon biopsy represents a sensitive method to monitor the severity of mucosal inflammation in patients affected by IBD;

hemorrhagic rectocolitis which is located only on rectum and colon.

Against the severe forms of IBD, various treatments allow the patients today to treat the symptomatic crisis and, to a lesser extent, to space them by using anti-inflammatory drugs; corticoids; immunosuppressive agents; biotherapies and surgery. Among anti-inflammatory drugs treatments, we can quote salicylated derivatives which induce less toxicity. Mesalazin is, according to current practice, the treatment which is administered at the beginning of the first inflammatory crisis. Then are used more powerful, but also more toxic anti-inflammatory drugs, such as cortisone. When these treatments appear ineffective; there is still the possibility to use a more recent therapeutic, such for Crohn's disease: a new treatment called Remicade™ which corresponds to a monoclonal antibody against TNF-α. This is a highly targeted drug but also very expensive which can, for example, treat crisis resistant to the treatment by cortisone, and maintain Crohn's disease in remission. As maintenance treatment, to prevent that the patient does not relapse, are used salicylated and immunosuppressive agents which depress immunity; the latter being over expressed in patients affected by one of the above diseases. Unfortunately, it is often necessary to resort to surgery in patients affected by one of these diseases: after eight to ten years of evolution, more than one patient out of two affected by Crohn's disease will be operated, firstly because it often appears shortenings of the intestine; sometimes, in approximately 20% of the cases, also abscesses can be located around the anus area. Among patients affected by hemorrhagic rectocolitis who are resistant to the treatment, there is then the resort to the surgery which consists in removing colon and rectum; this being a relatively heavy intervention. However, in subjects affected by Crohn's disease, surgery treats only the complications and does not prevent the disease from reappearing after the patient's operation.

The rheumatoid arthritis (RA) is an auto-immune disease of unknown precise origin; it is the most frequent cause of chronic polyarthritis. It represents the inflammatory type of rheumatism the most found in the adult. Its prevalence is evaluated between 0.3 and 0.8% according to the countries. It is characterized by an often bilateral and symmetrical articular attack, evolving by crisis to the deformation and the destruction of the attacked articulations. The disease generally starts by polyarthritis, i.e. inflammation of 4 or more articulations, characterized by scheduled inflammatory pain (wake up during the night, more than 30 minutes stretching during the morning), an articular stiffness, and a swelling called synovitis. Generally, the evolution, which lasts over several decades, is done by crisis, spaced by remissions of unpredicted rhythm and duration. During the crisis, most articulations are swollen and painful, and are associated with general signs (febricula, asthenia) and frequently with a biological inflammatory syndrome. The follow-up of the activity of the disease can be done using various scores. More used in clinical practice is the DAS 28, calculated starting from 4 parameters: the articular index (many painful articulations—except feet, ankles and hips not entered), the synovial index (many swollen articulations—except feet, ankles and hips), activity of the disease evaluated on a scale from 0 to 100 by the patient, and the sedimentation test. The symptomatic treatment can comprise the mere rest at the time of the crisis, the classic antalgic treatments, the non-steroidal anti-inflammatory drugs, the low dose corticosteroids, lower than 10 mg/day to restrict their side effects. Concerning the disease-modifying drugs and according to the severity of the disease, there exists currently a series of molecules which can be used such as in particular methotrexate; some immunosuppressors such as azathioprine or cyclosporine; anti-αTNF; CTLA4 inhibitor or anti-CD20. However, some of these molecules must be used with caution because of important side effects that they cause, or are not sufficiently effective in some patients, or then must be taken in association.

Multiple sclerosis (MS) is an inflammatory disease affecting the central nervous system. It involves, in particular, an inflammatory demyelination, a myelin destruction in the white substance of brain and marrow. Old lesions are the place when astrocytes proffer; characterizing sclerosis of the nervous tissue. These demyelinating lesions have a singular distribution and topography: not diffused but in plaques. Multiple forms that characterize the pathology renders it difficult for the family circle to understand, and is complex to diagnose it for the medical community. Current treatments aim at limiting frequency and extent of inflammatory crisis. They comprise two parts: a crisis treatment and a basic treatment. As crisis treatment, corticosteroids are sometimes prescribed as relay during approximately 3 weeks by oral route, associated with preventive measures in regard to the side effects of corticosteroids. As basic treatment, beta interferon and glatiramer acetate (copolymer of several amino-acids) are generally prescribed. In the severe forms, immunosuppressive agents such as mitoxantrone can be prescribed. Antibodies such as natalizumab (antibody against the a chain integrin of leucocytes) and Remicade™ (monoclonal anti-TNF-α) are also prescribed.

Psoriasis is a skin disease for which origin, partly genetic, is poorly known. This dermatological pathology affects between 1 and 3% of the population, indifferently women or men. There are several psoriasis types: psoriasis vulgaris, psoriasis eruptiva, psoriasis erythrodermic, psoriasis pustular, psoriatic arthritis. In its benign form, the psoriasis is limited to scalp, nails, knees, elbows, feet, hands and sometimes genitals. In the serious cases, it extends up to the whole body. This chronic dermatosis evolves in a very individual way, with eruptions, but also remissions during which the lesions disappear. Then, it is said that the psoriasis "is whitened". The respite is of duration very variable and the remission often incomplete. To date, no curative treatment allowing to recover completely from psoriasis is known; however it is possible to restrain psoriasis; to decrease the lesions extent and to improve patient's life. There are various types of treatment:

- a topical treatment for the non-severe form which consists in applying a cream containing corticosteroids, calcipotriene or tazarotene to the psoriasis area. These treatments have a favorable effect on psoriasis; unfortunately the plaques often reappear when the treatment stops. The last treatment generates also a form of desensitization, which obliges to increase doses with time. Moreover, the effect is not only topical if these pomades are applied to expanded area. This treatment form should thus be limited to acute or highly unaesthetic forms, during a short period and on a limited area;
- a phototherapy treatment. The solar exposure has generally a favorable influence on the psoriasis. However, in 10% of the cases, this exposure will be harmful. Then, the subject will have to avoid sun, or at least to avoid being directly exposed to its rays;
- a systemic treatment. For the most severe forms of psoriasis, the practitioner can prescribe a treatment to be administered orally or by injection. In this case, methotrexate, cyclosporine or anti-α TNF antibodies can be used. These treatments are called systemic because the drugs are intended to be disseminated in all the body. Often, they cause side effects, sometimes serious.

From these examples, it results that currently available treatments to cure autoimmune diseases are of limited number and appear sometimes very heavy and ineffective. This explains the importance of the research in this field. Several pharmaceutical laboratories and Universities develop drugs or treatments in the autoimmune diseases. We can quote as example, purine-containing treatments (FR2851248A and WO 96/18397A); anti-cytokine or anti-receptor antibodies (US 2003232009A, WO 06/121852, WO 06/092530, EP 1593393A and WO 07/009,065); vaccines or auto-antigens (WO 01/74375, EP 1621208A, WO 07/044,394), etc. These therapeutic molecules are still in basic research or clinical studies and it is difficult now to evaluate their efficiency in man.

The Applicant was interested in a thymulin analogue peptide active on the immune system and in the treatment of autoimmune diseases. It is known since the end of the 1950's that thymus plays a central role in the differentiation of T lymphocytes, which are responsible in particular of graft rejection and of the defense against viruses and certain bacteria. The hormone secreted by the thymus was then identified as a 9 amino-acids peptide: the thymuline (Bach, Pleau et al Immunol letters, 1979; 1: 179-182; Amor et al, Annals of the Rheumatic Disease 1987: 46: 549-554). Thymulin properties on the immune system were proved to be zinc-dependant. Indeed, zinc associated with peptide confers on this one a tetrahedral conformation which corresponds to the active form of the molecule. In the absence of zinc, thymulin has no more activity on immune system.

Thymulin analogue peptides of this invention were already described for the treatment of inflammatory and neurogenic pain (WO 03/030927); Saade et al., Neuroscience, 2003; 119 (1): 155-65, and Safieh-Garabedian et al., Br J. Pharmacol. 2002 July; 136 (6): 947-55. In the last publication, it is reported that peptide PAT confers analgesic and anti-inflammatory effects, from a series of experiments carried out in rats by endotoxin intraplantar (i.p1) and intraperitoneal (i.p) injections. Cytokines dosages were carried out on skin and liver tissue sampling. It is important to specify that these authors were not interested by intestinal inflammatory pain, or by the pain from rheumatoid arthritis. Moreover, the model used in the latter application can by no means be regarded as a model to study autoimmune and inflammatory diseases such as IBD (Crohn's disease, hemorrhagic rectocolitis) or rheumatoid arthritis. Indeed, in this study, capsaicin model was used as visceral pain model; it is a molecule which causes burn and pain feelings. It is important to specify that it acts on the sensory neurons level but not on inflammation itself. In an example, capsaicin is injected in rats which beforehand received or not PAT peptide; and nociception scores (painful perception) caused by capsaicin are quoted. Firstly, due to its model of action, capsaicin model is not pertinent in the investigation of autoimmune diseases such as IBD. Moreover, patent application WO 03/030927 does not refer specifically to autoimmune diseases such as IBD of which Crohn's disease or hemorrhagic rectocolitis.

The Applicant was interested by determining whether the PAT nonapeptide, for which harmlessness was established, can be regarded as a new drug to treat autoimmune diseases such as IBD, rheumatoid arthritis, multiple sclerosis or psoriasis.

SUMMARY OF THE INVENTION

The present invention refers to the use of the PAT nonapeptide responding to the formula (I):

EAKSQGGSD;

or one of its pharmaceutically acceptable salts in the preparation of a drug in the treatment of autoimmune diseases such as intestinal bowel diseases (IBD); rheumatoid arthritis, multiple sclerosis and psoriasis of which psoriatic arthritis.

Preferably, the present invention refers to IBD and even more preferentially to Crohn's disease.

According to another mode of realization, the present invention refers to the therapeutic use of the PAT peptide in the treatment of arthritis; the rheumatoid arthritis being the most preferred indication.

The PAT peptide is administered in man or in animal at a dose comprised between 0.1 and 50 mg; and preferentially between 1 and 10 mg.

By "pharmaceutically acceptable salt", one understands for example and in a nonrestrictive way an acetate, a sulfate or a hydrochloride.

The invention also relates to the use of a compound of formula (I) in which one or more amino-acid are in D configuration.

The pharmaceutical composition according to the invention is presented in a suitable form for an administration:
- by parenteral route, such as in the form of injectable preparations suitable for intraperitoneal, subcutaneous, intravenous or intramuscular route;
- by oral route, such in the form of pill coated or not, capsule, powder, pellets, suspension or oral solution. Such a form for the administration by oral route can confer immediate, prolonged or delayed release of the active principle. Such forms with prolonged or delayed release are described, for example, in the patent applications EP 253104 or EP 576643;
- by rectal route, such as for example, in the form of suppositories;
- by topical route, in particular transdermal such as in the form of patch, pomade or gel;
- by intranasal route, such as in the form of aerosols and sprays;
- by perlingual route;
- by intraocular route.

The pharmaceutically acceptable vehicle can be selected among vehicles currently used according to the mode of administration.

BRIEF DESCRIPTION OF THE DRAWINGS

Other advantages and characteristics of the invention will appear during the reading of the following examples. It will be referred to the annexed drawings in which:

FIG. 1 shows the effect of the PAT nonapeptide on animal weight in which colitis was induced by TNBS injection;

FIG. 2 illustrates the effect of PAT nonapeptide on the colon inflammation which was caused beforehand by the TNBS;

FIG. 3 shows the effect of PAT nonapeptide on TNF-α, IL-1β and IL-6 pro-inflammatory cytokines, and on IL-10 anti-inflammatory cytokine.

FIG. 4 shows the effect of PAT peptide (at two different doses) compared to that of a reference NSAID (indomethacin) on the volume of the leg in arthritic rats;

FIG. 5 shows the effect of PAT peptide (at two different doses) compared to that of a reference NSAID (indomethacin) on the macroscopic clinical score in arthritic rats;

FIG. 6 shows the effect of peptide PAT (at two different doses) compared to that of a reference NSAID (indomethacin) on the hypersensitivity measured by the plantar test in arthritic rats;

FIG. 7 shows the effect of peptide PAT (at two different doses) compared to that of a reference NSAID (indomethacin) on the globular sedimentation test in arthritic rats.

DETAILED DESCRIPTION OF THE INVENTION

Example 1

Effect of PAT Nonapeptide in a Mice Model of Crohn's Disease

Experimental Protocol

Synthesis of the Nonapeptide

Peptide was made on a solid phase according to a Foc/tu method; it was cleaved and deprotected by trifluoroacetic acid; then purified by reverse phase analytical and preparative high pressure liquid chromatography and freeze-dried. Its purity (>95%) and its identity were confirmed by analytical HPLC and mass spectrometry. Sequence of the nonapeptide: H EAKSQGGSD-NH$_2$ (SEQ ID NO:1) of 877 Da.

It should be noted that, during this synthesis, a particular attention was paid to reduce to the maximum a frequent by-product made by the transformation of the glutamine (Glu) into pyro-glutamine (Pyro-Glu), which involves the formation of the peptide PyroGlu-Ala-Lys-Ser-Glu-Gly-Gly-Ser-Asp (SEQ ID NO:2). This by-product could be reduced in the present invention by optimizing the synthesis conditions with acetate, by resuspending the peptide in saccharose and by storing the suitable product (at minus 20° C.). The synthesized product contains 1.68% of this contaminant.

Colitis Induction

The PAT nonapeptide was studied in animal model of experimental colitis. In mice, one of the clearly established IBD colitis models is the one in which the induction is performed by the use of trinitrobenzene sulphonic acid (TNBS). TNBS is a hapten which, when it is administered by intrarectal route, induced a severe colonic transmural inflammation; the induced effects present many similarities with those induced by Crohn's disease (Elson C O et al Experimental models of inflammatory bowel disease. Gastroenterology 2003; 10: 1344-67; Strober W et al., The immunology of mucosal models of inflammation. Annu Rev Immunol 2002; 20: 495-49).

Colitis is induced in C57BL/6J mice of 7-8 weeks old after TNBS administration per rectal route according to the protocol described by Sugimoto K. et al (Gastroenterology 2002: 123; 1912-1922). The administration is performed directly in the lumen of the colon (over a 3-4 cm length) by using a 1 ml-syringe and a polyethylene cannula (Intradermic PE-20, Becton Dickinson) of a 100 μl solution containing 2.5 mg of TNBS dissolved beforehand in 50 μl of ethanol. After the administration, the mice are maintained 30 seconds in vertical position.

Treatment

The design of the study is the following:
- one control batch of 5 mice treated by ethanol/PBS mixture (vol/vol):
- one test batch of 10 mice to which TNBS is administered (2.5 mg in 50% ethanol);
- one test batch of 10 mice to which TNBS and nonapeptide are administered with the amount of 1 μg/mouse;
- one test batch of 10 mice to which TNBS and nonapeptide are administered with the amount of 5, μg/mouse;
- one batch of 10 mice to which TNBS and nonapeptide are administered with the amount of 25 μg/mouse.

The PAT nonapeptide is administered by intraperitoneal route 30 minutes before the TNBS induction of colitis. Several mice (5 of each test batch; 2 of control batch) are sacrificed at day 1 after TNBS induction. The remaining mice (5 of each test batch; 3 of control batch) are sacrificed at day 3 after TNBS induction.

Measured Parameters

Animal Weight

The animals are weighed every day until the sacrifice.

Colon Inflammation

As soon as the animals are sacrificed, the colon is sampled and a macroscopic analysis is carried out.

Expression of IL-1β, IL-6 and TNF-α by Quantitative RT-PCR

At days 1 and 3 after TNBS induction, the animals are sacrificed and colons are sampled in order to proceed to an extraction of total RNAs.

The latter is carried out by denaturation with guanidine thiocyanate; cDNA synthesis is made starting from 1 ng of RNA using a kit (Euromedex). A quantitative PCR is carried out; the reaction is performed in a 25 μl final volume by using SYBR kit (Eurogentec). Stimulation rate is determined for each cytokine compared to reference cDNA which is that corresponding to 34B4 ribosomal phosphoprotein.

Results

Animal Weight

The results obtained in the FIG. 1 shows that TNBS injection by rectal route induces a notable slimming of the mice, and that administration beforehand of PAT nonapeptide allows to limit this weight loss especially at the dose of 25 μg/mouse. Doses of 1 μg and 5 μg/mouse do not show a significant effect.

Measure of Colon Inflammation

We have observed that PAT nonapeptide allows to reduce to a significant extent inflammation caused by TNBS rectal injection. According to the results shown in the FIG. 2, this effect is dose dependant and the maximal effect is observed for the dose of 25 μg/mouse. On average, the colon measures a length of 7 cm in control mice; 5 cm in TNBS-treated mice, and 6.5 cm in TBNS-PAT treated mice.

Pro-Inflammatory Cytokine Dosages

In the FIG. 3, we have observed that IL-1β cytokine expression is increased in TNBS treated mice of almost 50 fold. After the administration of 25 μg of PAT, it is noted that IL-1β expression decreases to a significant extent.

IL-6 expression is also strongly increased in TNBS-treated mice (around 30 fold). In the presence with 25 μg of PAT per mouse, IL-1β expression decreases to a significant extent.

Concerning TNF-α, its expression increases very slightly (around 4 fold) in TNBS-treated mice. When PAT is administered at a dose of 25 μg/mouse, we have observed that the increase is notably reduced.

Interestingly, we have noted in TNBS-treated mice, the level of IL-10 anti-inflammatory cytokines is not increased, whereas the beforehand administration of PAT at a dose of 25 μg/mouse causes a significant increase (more than 3 fold) of this cytokine.

As indicated above, intrarectal injected TNBS induces a severe colon inflammation. This one presents much similarity with symptoms induced by Crohn's disease, and in particular, on the pro-inflammatory cytokines secretion. These results associated with the ones before allow to assert that PAT nonapeptide is an excellent candidate in the treatment of autoimmune diseases such as IBD.

Example 2

Effect of the PAT in a Model of the Disease of Rheumatoid Arthritis in the Rat

Experimental Protocol

Model of Rheumatoid Arthritis

We used the model of arthritis induced by Freund' adjuvant as described in the article of Milan et al., J Neurosci 1986; 6: 899-906. The rats are administered with *Mycobacterium butyricum* develop usually a severe polyarthritis which resembles to that in human. Rats of OFA (SD) strain (Oncins France Strain A) weighing approximately 200 g received an 100 injection of a 10 mg/ml *Mycobacterium butyricum* solution at the articulation of the right ankle.

For all the measured parameters, the rats were divided into 5 groups (8 rats/group) in the following way:
reference group: the rats received a paraffin injection instead of the solution of *Mycobacterium butyricum* (no induced arthritis) then receive an intraperitoneal injection of saline solution;
arthritic group+injection of saline solution;
arthritic group+intraperitoneal injection of 3 mg/kg indomethacin; the indomethacin being a NSAID classically used as reference in this kind of test;
arthritic group+intraperitoneal injection of 0.4 mg/kg indomethacin;
arthritic group+intraperitoneal injection of 4 mg/kg indomethacin.

The products are administered 5 times per week during 3 weeks. At the beginning of the experimentation (day 0), one determines the initial values for the different parameters (volume of the leg, macroscopic clinical score, sedimentation test and hypersensitivity).

Measured Parameters

During the experiment, several parameters are measured:
the volume of the leg ("paw latency duration");
the globular sedimentation test ("Erythrocyte Sedimentation rate");
the macroscopic score:
   "0" means that no sign of arthritis was detected;
   "1" means that a swelling or an inflammation was detected on a leg;
   "2" means that a swelling or an inflammation was detected on two legs;
   "3" means that a swelling or an inflammation was detected on at lest 3 legs;
   "4" means that a swelling or an inflammation was detected on the 4 legs.
hypersensitivity according to the plantar test: carried out according to Yukinori Nagakura and al, *Allodynia and hyperalgesia in adjuvant-induced arthritic rats: time course of progression and efficacy of analgesics, JPET* 306: 490-497, 2003, or in Andersen M L and al "*Evaluation of acute and chronic treatments with Harpagophytum procumbens one Freund's adjuvant-induced arthritis in rats*". J. Ethnopharmacol. 2004 April; 91 (2-3): 325-30;
the erythrocyte sedimentation rate (ESR): the increase in this one generally accompanies the clinical symptoms met in induced arthritis. The ESR is measured in the arthritic rats (at Day 21) 1 hour and 2 hours after the injection of PAT or indomethacin, according to the protocol of Mahajan S G, et al., Protective Effect of Ethanolic Extract of Seeds of Moringa will oleifera Lam. Against Inflammation Associated with Development of Arthritis in Rats. J. Immunotoxicol. 2007 January; 4 (1): 39-47.

Results

In FIG. 4, we observe that from 10 days after the administration of *Mycobacterium butyricum*, the rats start to show signs of inflammation. In the reference rats, we do not observe notable variation in the volume of the leg (FIG. 4). The injection of the Freund's adjuvant causes an increasing swelling of the leg up to Day 19. The treatments of the animals by administration of PAT peptide or indomethacin do not have a notable effect during the first 12 days. On the other hand, from Day 14, these treatments cause a notable reduction of inflammation and of the volume of the leg; this reduction lasting until Day 21. Surprisingly, it should be noted that PAT peptide causes the same effect at the two doses 0.4 and 4 µg/kg; suggesting that there is no dose response relationship.

FIG. 5 shows the effect produced on the clinical macroscopic score after administration of PAT peptide compared to that produced after administration of indomethacin. It is observed that the disease is progressive in the arthritic rats which received saline solution, and that the score increases until Day 21. On the other hand, we notice a significant reduction in the macroscopic score in the arthritic rats which received PAT peptide or indomethacin when compared to arthritic rats which received that saline solution. As observed previously, PAT peptide intraperitoneally administered at the dose of 4 µg/kg shows less effects than when administered at the dose of 0.4 µg/kg.

FIG. 6 shows the results of the effect of the PAT on the hypersensitivity measured by the plantar test in the arthritic rats. At Day 0; the duration of latency is the same one for all the groups. At Day 16, w observe a very significant increase in hypersensitivity in the group of the untreated arthritic rats, whereas hypersensitivity is very reduced in the arthritic groups of rats treated by PAT peptide (at the 2 doses) and by indomethacin; this hypersensitivity being equivalent to that of the reference group (non-arthritic).

FIG. 7 shows the results of the erythrocyte sedimentation rate (ESR). The latter is rather high in arthritic rats. On the other hand, it is reduced in a very important way in arthritic rats treated by PAT peptide or by the NSAID indomethacin. We notice a more reduced ESR in the treated group at the dose of 0.4 µg/kg (when it is measured 1 hour after the injection), compared to the treated group by indomethacin, and is very similar to the ESR of the reference rats. Finally the treatment by a dose 10 fold higher of PAT (4 µg/kg) did not have a significant effect on the reduction of ESR.

CONCLUSIONS

Considering the different measured parameters, rats in which arthritis is induced by Mycobacterium generally develop a severe polyarthritis which resembles that which met in human. We notice that PAT peptide, at least at the dose of 0.4 µg/kg (i.p) makes it possible to reduce very significantly the progression of arthritis, and that its activity is detectable on various body parts (leg; peripheral hypersensitivity and erythrocyte sedimentation rate). Lastly, it is interesting to note that PAT peptide administered at the dose of 0.4 µg/kg (i.p.) shows at least a similar efficacy to that of the NSAID indomethacin administered at the dose of 3 mg/kg, so at a dose 7500 fold lower.

The invention claimed is:

1. A method of treating an autoimmune disease, comprising administering an effective amount of the PAT nonapeptide, $$\text{EAKSQGGSD,} \quad (\text{SEQ ID NO: 1})$$

or a pharmaceutically acceptable salt thereof, to a person in need thereof.

2. The method of claim 1, wherein the auto-immune disease is an intestinal bowel disease (IBD) arthritis, psoriasis, or multiple sclerosis.

3. The method of claim 2, wherein the IBD is the Crohn's disease.

4. The method of claim 2, wherein the arthritis is the rheumatoid arthritis.

5. The method of claim 1, wherein at least one amino-acid of the PAT nonapeptide is a D configuration.

6. The method of claim 1, wherein the PAT nonapeptide is in a form administrable by parenteral route, oral route, rectal route or any other acceptable route.

7. The method of claim 1, wherein the PAT nonapeptide is administered in a dose of between 0.1 mg and 50 mg.

8. The method of claim 1, wherein said PAT nanopeptide is administered in a composition comprising a pharmaceutically acceptable vehicle.

9. The method of claim 1, wherein the autoimmune disease is multiple sclerosis.

10. The method of claim 1, wherein the autoimmune disease is psoriasis.

\* \* \* \* \*

```
SEQUENCE LISTING

<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: Nonapeptide

<400> SEQUENCE: 1

Glu Ala Lys Ser Gln Gly Gly Ser Asp
1               5

<210> SEQ ID NO 2
<211> LENGTH: 9
<212> TYPE: PRT
<213> ORGANISM: Artificial sequence
<220> FEATURE:
<223> OTHER INFORMATION: Nonapeptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 2

Glu Ala Lys Ser Glu Gly Gly Ser Asp
1               5
```